(12) United States Patent
Xu et al.

(10) Patent No.: US 9,672,620 B2
(45) Date of Patent: Jun. 6, 2017

(54) RECONSTRUCTION WITH OBJECT DETECTION FOR IMAGES CAPTURED FROM A CAPSULE CAMERA

(71) Applicant: Capso Vision, Inc., Saratoga, CA (US)

(72) Inventors: Yi Xu, Menlo Park, CA (US); Chenyu Wu, Sunnyvale, CA (US); Kang-Huai Wang, Saratoga, CA (US)

(73) Assignee: CAPSOVISION INC, Saratoga, CA (US)

(*) Notice: Subject to any disclaimer, the term of this patent is extended or adjusted under 35 U.S.C. 154(b) by 125 days.

(21) Appl. No.: 14/827,325

(22) Filed: Aug. 15, 2015

(65) Prior Publication Data
US 2017/0046825 A1    Feb. 16, 2017

(51) Int. Cl.
*G06K 9/00*   (2006.01)
*G06T 7/00*   (2017.01)
(Continued)

(52) U.S. Cl.
CPC ........ *G06T 7/0014* (2013.01); *A61B 1/00009* (2013.01); *A61B 1/041* (2013.01); *G06T 5/006* (2013.01); *G06T 7/003* (2013.01); *G06T 7/0036* (2013.01); *G06T 7/0081* (2013.01); *G06T 7/0097* (2013.01); *G06T 11/60* (2013.01); *H04N 5/2252* (2013.01); *H04N 5/23229* (2013.01); *H04N 5/247* (2013.01); *H04N 5/265* (2013.01); *G06T 2207/10068* (2013.01); *G06T 2207/20048* (2013.01); *G06T 2207/20072* (2013.01); *G06T 2207/20081* (2013.01);
(Continued)

(58) Field of Classification Search
CPC ..... G06T 7/003; G06T 7/0014; G06T 7/0036; G06T 7/0081; G06T 7/0097; G06T 5/006; G06T 2207/10068; G06T 2207/20048; G06T 2207/20072; G06T 2207/20081; G06T 2207/20148; G06T 2207/20221; G06T 2207/30028
See application file for complete search history.

(56) References Cited

U.S. PATENT DOCUMENTS

| 8,422,755 B2* | 4/2013 | Drozdzal | G06T 7/38 348/715 |
| 8,771,176 B2* | 7/2014 | Hendriks | A61B 1/00188 600/167 |

(Continued)

*Primary Examiner* — Shefali Goradia
(74) *Attorney, Agent, or Firm* — Blairtech Solution LLC (57) ABSTRACT

A method of processing images captured using a capsule camera is disclosed. According to one embodiment, two images designated as a reference image and a float image are received, where the float image corresponds to a captured capsule image and the reference image corresponds to a previously composite image or another captured capsule image prior to the float image. Automatic segmentation is applied to the float image and the reference image to detect any non-GI (non-gastrointestinal) region. The non-GI regions are excluded in match measure between the reference image and a deformed float image during the registration process. The two images are stitched together by rendering the two images at the common coordinate. In another embodiment, large area of non-GI regions are removed directly from the input image, and remaining portions are stitched together to form a new image without performing image registration.

23 Claims, 3 Drawing Sheets

(51) Int. Cl.
    A61B 1/00      (2006.01)
    A61B 1/04      (2006.01)
    G06T 11/60     (2006.01)
    H04N 5/225     (2006.01)
    H04N 5/232     (2006.01)
    H04N 5/247     (2006.01)
    H04N 5/265     (2006.01)
    G06T 5/00      (2006.01)

(52) U.S. Cl.
    CPC .......... *G06T 2207/20148* (2013.01); *G06T 2207/20221* (2013.01); *G06T 2207/30004* (2013.01); *G06T 2207/30028* (2013.01)

(56) References Cited

U.S. PATENT DOCUMENTS

| | | | |
|---|---|---|---|
| 2009/0010507 A1 | 1/2009 | Geng | |
| 2010/0268025 A1* | 10/2010 | Belson | A61B 1/00158 600/109 |
| 2011/0305377 A1 | 12/2011 | Orozdzal et al. | |
| 2013/0002842 A1* | 1/2013 | Das | H04N 7/18 348/65 |
| 2015/0221116 A1 | 8/2015 | Wu et al. | |
| 2016/0037082 A1* | 2/2016 | Wang | A61B 1/00009 348/65 |

* cited by examiner

RECONSTRUCTION WITH OBJECT DETECTION FOR IMAGES CAPTURED FROM A CAPSULE CAMERA

CROSS REFERENCE TO RELATED APPLICATIONS

The present invention is related to PCT Patent Application Serial No. PCT/US14/38533, filed on May 19, 2014, which claims priority to U.S. Provisional Patent Application No. 61/828,653, filed on May 29, 2013. The U.S. Provisional Patent Application and PCT Patent Application are hereby incorporated by reference in their entireties.

FIELD OF THE INVENTION

The present invention relates to deriving composite images from images captured using in vivo capsule camera.

BACKGROUND AND RELATED ART

Devices for imaging body cavities or passages in vivo are known in the art and include endoscopes and autonomous encapsulated cameras. Endoscopes are flexible or rigid tubes that pass into the body through an orifice or surgical opening, typically into the esophagus via the mouth or into the colon via the rectum. An image is formed at the distal end using a lens and transmitted to the proximal end, outside the body, either by a lens-relay system or by a coherent fiber-optic bundle. A conceptually similar instrument might record an image electronically at the distal end, for example using a CCD or CMOS array, and transfer the image data as an electrical signal to the proximal end through a cable. Endoscopes allow a physician control over the field of view and are well-accepted diagnostic tools. However, they do have a number of limitations, present risks to the patient, and are invasive and uncomfortable for the patient. Their cost restricts their application as routine health-screening tools.

An alternative in vivo image sensor that addresses many of these problems is capsule endoscope. A camera is housed in a swallowable capsule along with a radio transmitter for transmitting data to a base-station receiver or transceiver. A data recorder outside the body may also be used to receive and record the transmitted data. The data primarily comprises images recorded by the digital camera. The capsule may also include a radio receiver for receiving instructions or other data from a base-station transmitter. Instead of radio-frequency transmission, lower-frequency electromagnetic signals may be used. Power may be supplied inductively from an external inductor to an internal inductor within the capsule or from a battery within the capsule.

In an autonomous capsule system, multiple images along with other data are collected during the course when the capsule camera travels through the gastrointestinal (GI) tract. The images and data after being acquired and processed are usually displayed on a display device for a diagnostician or medical professional to examine. However, each image only provides a limited view of a small section of the GI tract. It is desirable to form (stitch) a single composite image or a small number of composite images with a larger field of view from multiple capsule images. A large image can take advantage of the high-resolution large-screen display device to allow a user to visualize more information at the same time. An image stitching process may involve removing redundant overlapped areas between images so that a larger area of the inner GI tract surface can be viewed at the same time in a single composite image. A larger image can provide a broader view of a significant portion of the inner GI tract surface.

However, in typical capsule images from the GI tract, there are a lot of non-GI objects such as bubbles and debris that will affect image registration, which is a crucial step in image stitching to transform multiple images into one common coordinate system. Subsequently, these non-GI objects will affect the quality of image stitching. Therefore, it is desirable to develop a method that may identify such non-GI objects and takes it into consideration in image registration to improve the accuracy.

SUMMARY OF THE INVENTION

A method of processing images captured using a capsule camera is disclosed. According to one embodiment, two images designated as a reference image and a float image are received, where the float image corresponds to a captured capsule image and the reference image corresponds to a previously composite image or another captured capsule image prior to the float image. The float image is automatically segmented into one or more first native GI regions if any native GI sample is detected for the float image and one or more first non-GI regions if any non-GI sample is detected for the float image. The reference image is automatically segmented into one or more second native GI regions if any native GI sample is detected for the reference image and one or more second non-GI regions if any non-GI sample is detected for the reference image. The float image is then registered with respect to the reference image by optimizing a match measure between the reference image and a deformed float image with said one or more first non-GI regions and said one or more second non-GI regions excluded from computing the match measure between the reference image and a deformed float image. The deformed float image is generated by applying a transformation model to the float image to adjust geometric deformation between the float image and the reference image. Finally, a composite image is generated by rendering the reference image and the deformed float image after said registering the float image with respect to the reference image.

The non-GI samples may correspond to bubbles, debris or feces in the human GI tract. The match measure between the reference image and the deformed float image is scaled according to the number of native GI pixels included in the match measure. The transformation model may correspond to a free-form deformation cubic B-splines, Radial Basis Functions, Discrete Fourier/Cosine Transformation Bases, or other deformation models.

The float image or the reference image can be segmented using segmentation process based on pixel intensity values and/or similarities among neighboring pixels. In this case, the segmentation process generates respective one or more irregular-shaped first regions or second regions of non-GI pixels if any non-GI sample is detected for the float image or the reference image respectively.

The float image or the reference image can also be segmented using sliding window classification to derive respective one or more regular-shaped first regions or second regions of non-GI pixels if any non-GI sample is detected for the float image or the reference image respectively. The shape of the sliding window can be a rectangle, a circle, a hexagon, etc. In this case, the sliding window classification utilizes a high-level feature descriptor derived from a group of candidate descriptors consisting of histogram of oriented gradient, color histogram, color moments, and other features. The feature descriptor associated with object detection can be one of the candidate descriptors or a combination of more than one candidate descriptors. Furthermore, segmentation process for the float image or the reference image includes training a machine learning engine, where the high-level feature descriptors and labels associated with each image sample in each sliding window are provided to the machine learning algorithm to train a classifier. The labels may correspond to object category of each image sample. During actual processing of new images, feature descriptor is computed on each sample from each sliding window location on an image and provided to the classifier to predict the object category of each sliding window.

The optimizing the match measure between the reference image and the deformed float image may correspond to minimizing mean square error (MSE) measure or maximizing mutual information (MI) measure between the reference image and the deformed float image. The result of the optimizing is a deformation model that transforms the float image to the same coordinate system as the reference image.

The system may further comprise process of determining one or more over-exposure regions in the float image, the reference image, or both if any over-exposed region is detected in the float image, the reference image, or both respectively. The process of optimizing the match measure between the reference image and the deformed float image will exclude the over-exposure regions. The approaches described for excluding non-GI regions can be adapted for excluding over-exposure regions. Other imaging artifacts, such as ghosting, may also be detected and processed similarly.

If the optimized measure satisfy a condition (e.g., the error measure is smaller than a threshold), the deformed float image and reference image are composed together in the same coordinate using image stitching. If two corresponding pixels in the float image and the reference image are both native GI pixels or both non-GI pixels, a combination of the two corresponding pixels is used to generate composite pixel of the composite image. If two corresponding pixels in the float image and the reference image correspond to one native GI pixel and one non-GI pixel, the native GI pixel of the two corresponding pixels is used to generate composite pixel of the composite image.

In another embodiment, image stitching may be performed without image registration. If a majority area of the image corresponds to non-GI regions, the non-GI regions are directly removed from the image and remaining portions of the image corresponding to said one or more first native GI regions are used for said generating the composite image. The stitching may be done by placing the remaining portions of the float image and a previous composite image side by side. A blending may be applied to a band around each border between two portions to reduce transition artifacts from a portion to another.

DETAILED DESCRIPTION OF THE INVENTION

It will be readily understood that the components of the present invention, as generally described and illustrated in the figures herein, may be arranged and designed in a wide variety of different configurations. Thus, the following more detailed description of the embodiments of the systems and methods of the present invention, as represented in the figures, is not intended to limit the scope of the invention, as claimed, but is merely a representative of selected embodiments of the invention. References throughout this specification to "one embodiment," "an embodiment," or similar language mean that a particular feature, structure, or characteristic described in connection with the embodiment may be included in at least one embodiment of the present invention. Thus, appearances of the phrases "in one embodiment" or "in an embodiment" in various places throughout this specification are not necessarily all referring to the same embodiment.

Furthermore, the described features, structures, or characteristics may be combined in any suitable manner in one or more embodiments. One skilled in the relevant art will recognize, however, that the invention can be practiced without one or more of the specific details, or with other methods, components, etc. In other instances, well-known structures, or operations are not shown or described in detail to avoid obscuring aspects of the invention. The illustrated embodiments of the invention will be best understood by reference to the drawings, wherein like parts are designated by like numerals throughout. The following description is intended only by way of example, and simply illustrates certain selected embodiments of apparatus and methods that are consistent with the invention as claimed herein.

A review of general technical approaches to image registration and stitching can be found in "Image Alignment and Stitching: A Tutorial", by Szeliski, Microsoft Research Technical Report MSR-TR-2004-92, Dec. 10, 2006.

In image registration, corresponding features, objects or areas from two images are detected and identified first. Then two images can be aligned by warping one image to another.

One type of registration technique often used is the pixel-based registration, where a direct match is performed by comparing similarity of two image areas based on image intensity. There are several similarity measurements that can be used for evaluating the quality of pixel-based registration, such as sum of squared distance (SSD), normalized cross correlation (NCC), mutual information (MI), etc. For example, the mutual information can match images from two different modalities, where the MI of images A and B is defined as:

$$I(A, B) = \sum_{a,b} p(a, b) \log\left(\frac{p(a, b)}{p(a)p(b)}\right). \quad (1)$$

The mutual information measures the distance between the joint distribution of the images intensity values p(a,b) and the individual distributions of the images, p(a)p(b). The joint distribution, p(a,b) corresponds to probability that image A has an intensity value a and image B has an intensity value b. On the other hand, individual distribution p(a) corresponds to the probability that image A has an intensity value a, and individual distribution p(b) corresponds to the probability that image B has an intensity value b. The MI is a measure of dependence between two images. The assumption is that there is maximal dependence between the intensity values of the images when they are correctly aligned. Mis-registration will result in a decrease in the measure of mutual information. Therefore, larger mutual information implies more reliable registration.

Another type of registration technique often used is the feature-based registration, where a set of feature points in each image is determined first and the corresponding features of two images are then compared. To match two image patches or features captured from two different viewing angles, an affine camera model including scaling, rotation, etc., can be estimated based on the correspondences. To match two images of a moving object captured at two different time instances, a non-rigid model can be used.

The number of feature points is usually much smaller than the number of pixels of corresponding images. Therefore, the computational load for feature-based image registration is substantially less than that of pixel-based image matching. However, it is still time consuming for pair-wise matching. Usually k-d tree, a well-known technique in this field, is utilized to speed up this procedure. Nevertheless, feature-based image registration may not work well for images under some circumstances such as in-vivo images with fewer features. In this case, the direct image registration can serve as a main role and a combination of the above two approaches may be preferred.

Objects such as the in-vivo images of the GI tract captured by a capsule camera in the scene may be deformed and lack of distinguishable features. In one embodiment of the present invention, an intensity-based deformable registration framework is used. The transformation model can be free-form deformation cubic B-splines, Radial Basis Functions, or other models. Gradient-based method or other standard optimization approach can be used for optimizing the measure. In this disclosure, an initial frame or a previously stitched frame is referred as reference image R, and a next frame or a new frame to be added to the reference image is referred as float image F. The deformable registration deforms the float image F until it matches reference R. On the other hand, reference R is left unchanged.

For capsule images captured during the course of travelling through the GI tract, the situation is even more challenging. Not only the scenes corresponding to walls of the GI tract may be deformed and often are lack of distinguishable features, but also there may be non-GI objects such as bubbles and debris that are under motions independent of the GI tract. In addition, light reflection from near objects may cause over exposure for some parts of the image. There are other imaging artifacts, such as ghosting, can adversely affect the image registration process as well.

A method is disclosed in the present invention to overcome the issues mentioned. In one embodiment, a plurality of images captured by the camera is received and the non-native GI objects of the images are identified. The non-native GI objects refer to foreign objects such as bubbles, debris, feces, etc. The non-native GI objects are also called non-GI objects in this disclosure. During the optimization step of image registration, pixels corresponding to these non-native GI objects are excluded from the computation of the error measurement or similarity measurements.

Figure 1:
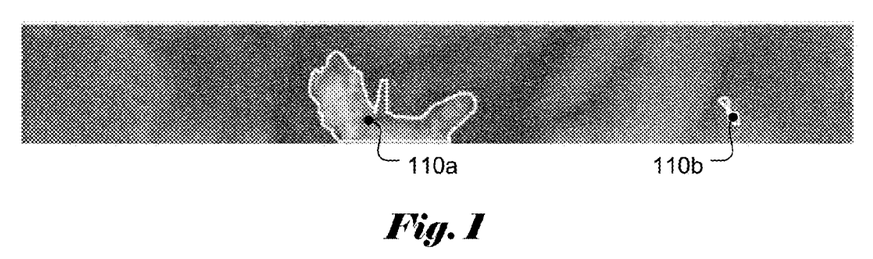
FIG. 1 illustrates an example of detecting native GI/non-GI regions using a segmentation algorithm based on color information of a pixel and/or its neighboring pixels, where the detected non-GI regions are indicated by contours of the detected non-GI regions.

One aspect of the invention addresses various approaches of segmentation of the non-GI objects. In one embodiment, a segmentation algorithm can label each pixel as GI or non-GI according to intensity values and/or similarities among neighboring pixels. This segmentation process will result in a set of irregular shaped connected regions of non-GI pixels. Pixels within each connected region will be excluded from similarity or error metric computation. FIG. 1 illustrates an example of non-GI object detection according to an embodiment of the present invention. The thick-lined contours in FIG. 1 indicate the boundaries (110a and 110b) of connected components of non-GI pixels.

Figure 2:
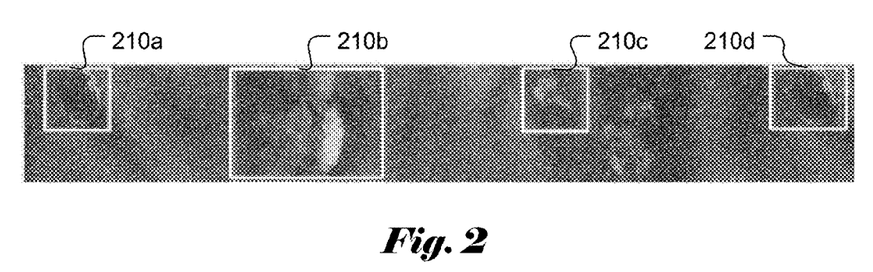
FIG. 2 illustrates an example of detecting native GI/non-GI regions using sliding window classification, where feature descriptors are computed on a pre-defined set of sliding windows with varying sizes and the detected non-GI regions are indicated by rectangles around the detected non-GI regions.

In another embodiment, non-GI object detection is based on regular-shaped image patches, where each image patch is classified as a GI object or non-GI object as a whole. The shape of the image patch can be rectangular, circle, hexagon, etc. Sliding window classification is a technique widely used in object detection. Each sliding window is a regular shaped region of interest from the input image. During the data preparing stage, a human operator labels a large amount of windows as GI or non-GI regions. The sliding window classification utilizes a high-level feature descriptor derived from a group of candidate descriptors consisting of histogram of oriented gradient, color histogram, color moments, and other features. The feature descriptor associated with object detection can be one of the candidate descriptors or a combination of more than one candidate descriptors. Furthermore, segmentation process for the float image or the reference image includes training a machine learning classifier (e.g. support vector machine (SVM) or random forest technique), where the high-level feature descriptors and labels associated with each image sample in each sliding window are provided to the machine learning algorithm to train a classifier. The labels may correspond to object category of each image sample. During actual processing of new images, feature descriptor is computed on each sample from each sliding window location of a new image and provided to the classifier to predict the object category. FIG. 2 illustrates an example of rectangular non-GI regions (210a, 210b, 210c and 210d) identified using the sliding window classification technique.

For image registration between reference R and floating image F, mean square error (MSE) can be used, where the MSE is defined as:

$$MSE = \frac{1}{mn}\sum_{i=0}^{m-1}\sum_{j=0}^{n-1} \|F''(i, j) - R(i, j)\|^2, \quad (2)$$

where (i,j) is a pixel coordinate. In the above measure, F'''(i,j) corresponds to a deformed version of the float image F(i,j) in order to take into consideration of deformation. During image stitching, the deformed float image and reference image are composed together in the same coordinate.

As mentioned earlier, an embodiment of the present invention takes into consideration of the non-GI objects during object detections by excluding non-GI pixels in the similarity or error metric computations. Accordingly, an example of error metric computation incorporating an embodiment of the present invention is modified as:

$$MSE = \frac{1}{C}\sum_{i=0}^{m-1}\sum_{j=0}^{n-1}\|F''(i,j) - R(i,j)\|^2 \cdot M(i,j), \quad (3)$$

$$\text{where, } M(i,j) = \begin{cases} 0, & (i,j) \text{ is non-GI in } F''' \text{ or } R \\ 1, & \text{otherwise} \end{cases}.$$

The variable C in equation (3) corresponds to the total number of pixels classified as GI pixels in the summation. However, when the non-GI regions are substantial, it may not be worthwhile or proper to register the current image with a reference image. Instead, in this case, only the remaining parts of the current image is used for composing images. For example, the remaining parts can be placed sided by side to form a size-reduced current image. Accordingly, an optional test can be applied to check whether said one or more first non-GI regions satisfy a condition. For example, the condition may correspond to whether said one or more first non-GI regions exceeds x percent of the image. If so, the non-GI regions can be deleted from the current image and the remaining smaller parts are used for image composition with a previous composite image, where substantial non-GI regions have been deleted as well. For example, the threshold can be set to 50% (i.e., x=50). However, a higher threshold, such as x=80, may also be used. Furthermore, a system may select a threshold from a list such as {50, 55, 60, 65, 70, 75, 80, 85, 90, 95}. If the condition is not met, the current float image is registered with respect to a reference image. During registration, the non-GI regions are excluded from the match measure between the current image and the reference image, where the reference image may correspond to a previously composite image.

Figure 3:
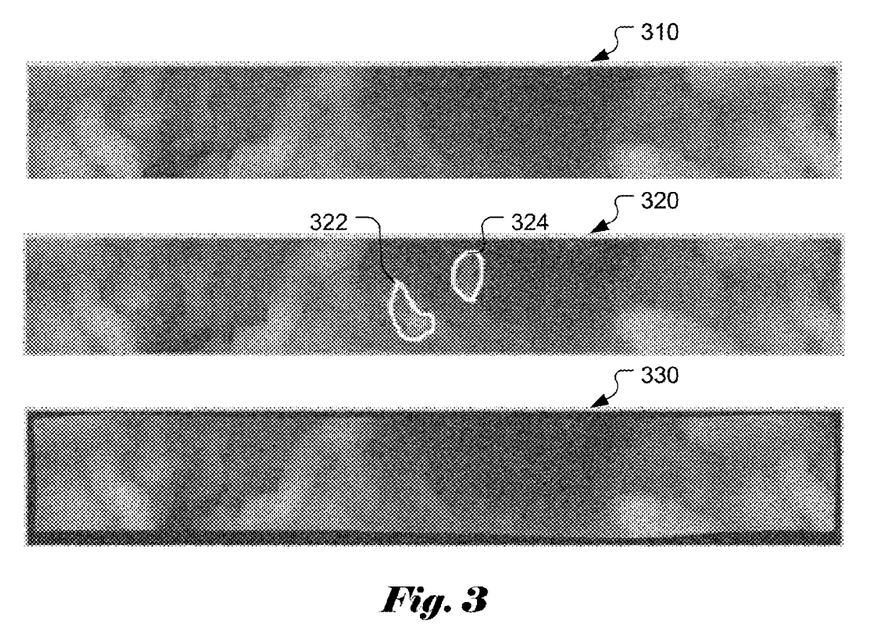
FIG. 3 illustrates an example of excluding non-GI regions detected in one of the images from image registration and generating a composite image based on transforming the float image to the coordinate of the reference image and compositing two images at the common coordinate, where the result composite does not contain non-GI object.

One aspect of the invention is related to image stitching. After image registration, the float image F''' and reference image R are composed together. If a pixel (i,j) is a GI pixel in only one image from F''' or R, then the GI pixel is chosen for pixel (i,j). If (i,j) is a GI pixel in both F''' and R, then a combination of F''' (i,j) and R (i,j) is used. If (i,j) is a non-GI pixel in both F''' and R, then a combination of F (i,j) and R (i,j) is used as well. FIG. 3 illustrates an example of stitching two images together with one of them containing detected non-GI regions. In FIG. 3, image 310 corresponds to a reference image, image 320 corresponds to a float image with two non-GI regions (322 and 324). The two images are stitched into one image (330).

Figure 4:
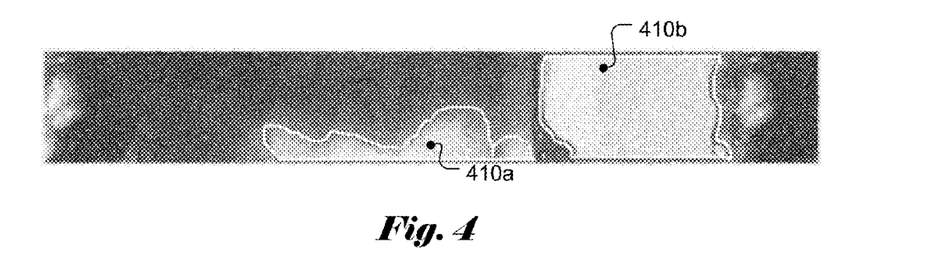
FIG. 4 illustrates an example of detecting over-exposed regions and excluding the over-exposed regions from the match measure during registration, where the detected over-exposed regions are indicated by contours of the detected over-exposed regions.

One aspect of the invention is related to the issue of over exposure for some parts of the capsule images. When the capsule is very close to an object, light reflection can cause over exposure. If the same part of the object is not over exposed in another image, the over-exposed part will contribute adversely to the error metric computation during image registration. In such cases, object detection developed for detecting non-GI object can be adapted to detect over exposed regions and exclude them from image registration. The object detection can also be adapted to detect other imaging artifacts such as ghosting, etc. FIG. 4 illustrates an example of over-exposed regions (410a and 410b) detected in a capsule image.

Figure 5:
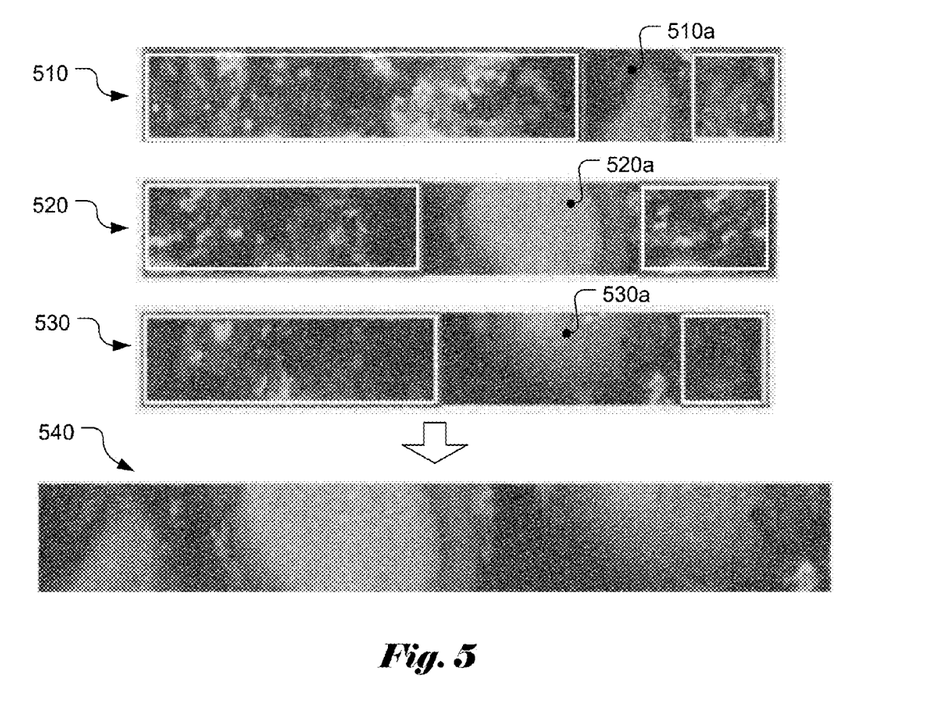
FIG. 5 illustrates an example of directly removing large non-GI regions and generating a composite image based on remaining native GI regions of the images.

One aspect of the invention is related to dealing with large area of unwanted pixels in the capsule images. When the majority of a capsule image consists of non-GI pixels (e.g. feces), these pixels can be removed directly and the remaining small portions can be stitched together onto a large picture without image registration. For example, in a sequence consisting 10 images, if only 1/10 of each image contains GI pixels, then only 1 frame will be produced while stitching preserves all GI pixels in this sequence. This procedure can be applied on irregular shaped non-GI regions or regular shaped non-GI regions produced by sliding window classification. If the percentage of non-GI pixels within an image exceeds a threshold (e.g., 50%), the non-GI regions are deleted from the original picture. Equivalently, the percentage of the GI pixels can be determined. If it is smaller than a threshold, the non-GI regions are directly deleted from the original picture. Other conditions may also be checked to determine whether to delete the regions of non-GI pixels directly. FIG. 5 illustrates an example of directly removing large non-GI regions and generating a composite image based on remaining native GI regions of the images. In FIG. 5, native GI regions (510a, 520a and 530a) are identified in three input images (510, 520 and 530). The native GI regions (510a, 520a and 530a) are used to form the composite image (540).

Figure 6:
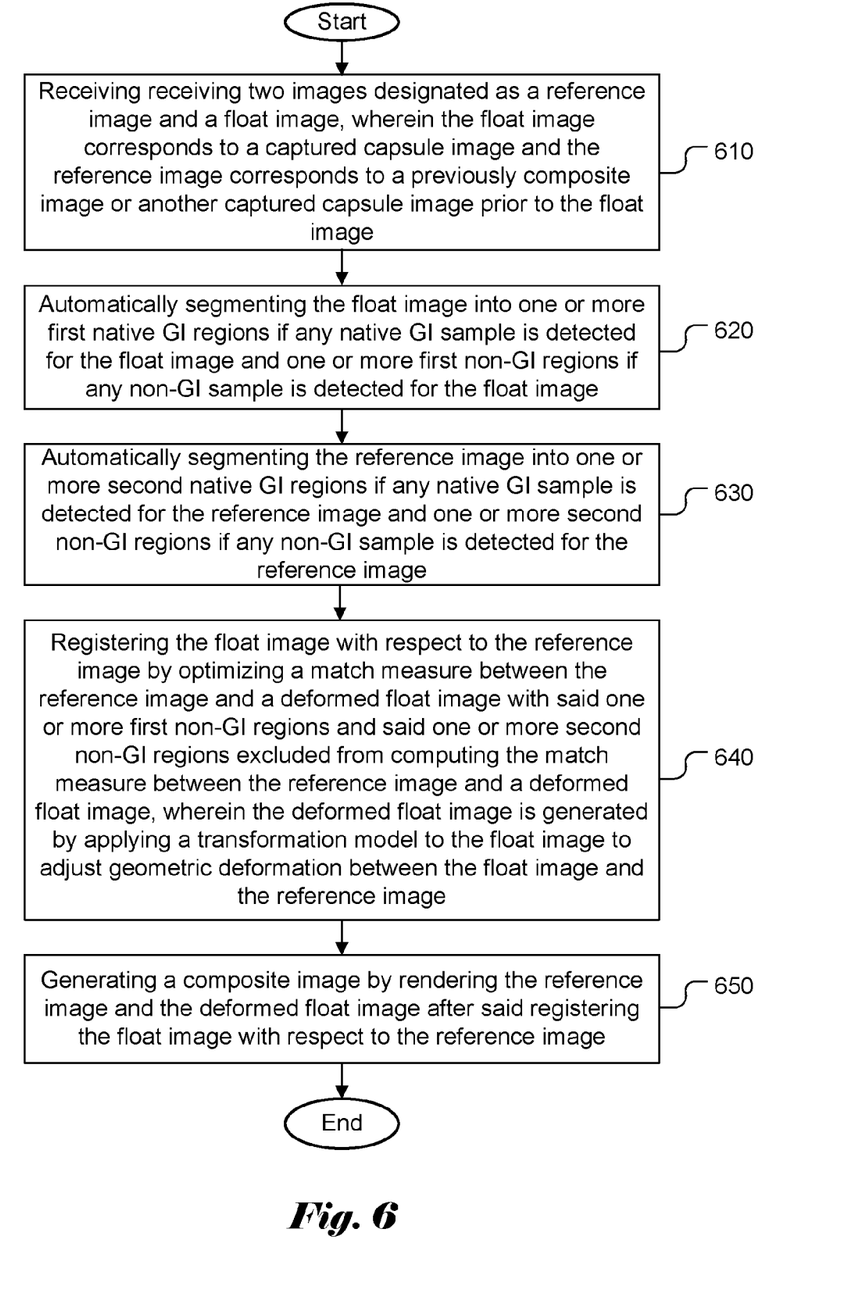
FIG. 6 illustrates an exemplary flowchart of an image processing system incorporating an embodiment of the present invention, where non-GI regions are identified and are excluded from the match measure for registration or directly removed.

FIG. 6 illustrates an exemplary flowchart of an image processing system incorporating an embodiment of the present invention, where non-GI regions are identified and are excluded from the match measure for registration. The system receives two images designated as a reference image and a float image as shown in step 610, wherein the float image corresponds to a captured capsule image and the reference image corresponds to a previously composite image or another captured capsule image prior to the float image. The float image is automatically segmented into one or more first native GI regions if any native GI sample is detected for the float image and one or more first non-GI regions if any non-GI sample is detected for the float image in step 620. The reference image is automatically segmented into one or more second native GI regions if any native GI sample is detected for the reference image and one or more second non-GI regions if any non-GI sample is detected for the reference image in step 630. Then, the float image is registered with respect to the reference image by optimizing a match measure between the reference image and a deformed float image with said one or more first non-GI regions and said one or more second non-GI regions excluded from computing the match measure between the reference image and a deformed float image in step 640. The deformed float image is generated by applying a transformation model to the float image to adjust geometric deformation between the float image and the reference image. If the measure satisfy a condition (e.g., error measure is smaller than a threshold), the composite image is generated by rendering the reference image and the deformed float image in a common coordinate after said registering the float image with respect to the reference image in step 650.

The invention may be embodied in other specific forms without departing from its spirit or essential characteristics. The described examples are to be considered in all respects only as illustrative and not restrictive. Therefore, the scope of the invention is indicated by the appended claims rather than by the foregoing description. All changes which come within the meaning and range of equivalency of the claims are to be embraced within their scope.

The invention claimed is:

1. A method of processing images of human gastrointestinal (GI) tract captured using a capsule camera, the method comprising:
   receiving two images designated as a reference image and a float image, wherein the float image corresponds to a current capsule image and the reference image corresponds to a previously composite image or another captured capsule image prior to the float image;
   automatically segmenting the float image into one or more first native GI regions if any native GI sample is detected for the float image and one or more first non-GI regions if any non-GI sample is detected for the float image;
   automatically segmenting the reference image into one or more second native GI regions if any native GI sample is detected for the reference image and one or more second non-GI regions if any non-GI sample is detected for the reference image;
   registering the float image with respect to the reference image by optimizing a match measure between the reference image and a deformed float image with said one or more first non-GI regions and said one or more second non-GI regions excluded from computing the match measure between the reference image and a deformed float image, wherein the deformed float image is generated by applying a transformation model to the float image to adjust geometric deformation between the float image and the reference image; and
   generating a composite image by rendering the reference image and the deformed float image in a common coordinate after said registering the float image with respect to the reference image.

2. The method of claim 1, wherein the float image or the reference image is segmented using segmentation process based on pixel intensity values and/or similarities among neighboring pixels.

3. The method of claim 2, wherein the segmentation process generates respective one or more irregular-shaped first regions or second regions of non-GI pixels if any non-GI sample is detected for the float image or the reference image respectively.

4. The method of claim 1, wherein the float image or the reference image is segmented using sliding window classification to derive respective one or more regular-shaped first regions or second regions of non-GI pixels if any non-GI sample is detected for the float image or the reference image respectively.

5. The method of claim 4, wherein the sliding window segmentation utilizes one or more high-level feature descriptors selected from a group of candidate descriptors including histogram of oriented gradient, color histogram, and color moments and other feature descriptors, for each sliding window associated with object detection of non-GI samples.

6. The method of claim 5, wherein said automatically segmenting the float image or said automatically segmenting the reference image includes machine learning and wherein the high-level feature descriptors and labels associated with each sample in each sliding window location of a set of sample images is provided to a machine learning algorithm to train a classifier.

7. The method of claim 6, wherein the labels correspond to an object category associated with said image sample in each sliding window.

8. The method of claim 1, wherein the match measure between the reference image and the deformed float image is scaled according to a number of native GI pixels included in the match measure.

9. The method of claim 1, wherein said optimizing the match measure between the reference image and the deformed float image corresponds to minimizing mean square error (MSE) measure, maximizing mutual information (MI) measure or minimizing/maximizing other measures between the reference image and the deformed float image.

10. The method of claim 1, further comprising determining one or more over-exposure regions or other imaging artifact in the float image, the reference image, or both if any over-exposed pixel or other imaging artifact is detected in the float image, the reference image, or both respectively, and wherein said optimizing the match measure between the reference image and the deformed float image further excludes said one or more over-exposure regions or other imaging artifact.

11. The method of claim 1, wherein the non-GI samples correspond to bubbles, debris or feces in the human GI tract.

12. The method of claim 1, wherein the transformation model corresponds to a free-form deformation cubic B-splines, Radial Basis Functions or other deformation models.

13. The method of claim 1, wherein if two corresponding pixels in the float image and the reference image are both the native GI pixels or both the non-GI pixels, a combination of said two corresponding pixels is used to generate composite pixel of the composite image.

14. The method of claim 1, wherein if two corresponding pixels in the float image and the reference image correspond to one native GI pixel and one non-GI pixel, the native GI pixel of said two corresponding pixels is used to generate composite pixel of the composite image.

15. The method of claim 1, further comprising generating a composite image based on the float image with said one or more first non-GI regions deleted and a previous composite image if said one or more first non-GI regions satisfy a first condition.

16. The method of claim 15, wherein the first condition corresponds to said one or more non-GI regions being larger than a threshold percentage within an image.

17. The method of claim 16, wherein the threshold percentage corresponds to x percent or larger and x is selected from a threshold group consisting of 50, 55, 60, 65, 70, 75, 80, 85, 90 and 95.

18. The method of claim 1, wherein said generating a composite image by rendering the reference image and the deformed float image in a common coordinate after said registering the float image with respect to the reference image is performed if said registering the float image with respect to the reference image satisfy a second condition.

19. The method of claim 18, wherein said second condition corresponds to an error measure between a deformed float image and the reference image being smaller than a first threshold, or a mutual information (MI) measure between the deformed float image and the reference image being greater than a second threshold.

20. A method of processing images of human gastrointestinal (GI) tract captured using a capsule camera, the method comprising:
   receiving a current image;
   automatically segmenting the current image into one or more native GI regions if any native GI sample is detected for the current image and one or more non-GI regions if any non-GI sample is detected for the current image; and if said one or more non-GI regions satisfy a condition, generating a current composite image based on the current image with said one or more non-GI regions deleted and a previous composite image; and wherein blending is applied to an area between the current image with said one or more non-GI regions deleted and the previous composite image.

21. The method of claim 20, wherein the condition corresponding to an area of said one or more non-GI regions exceeds a threshold.

22. The method of claim 20, wherein said generating the current composite image corresponds to placing remaining portions of the current image with said one or more non-GI regions deleted and a previous composite image side by side.

23. The method of claim 22, wherein blending is applied to a band around each border between two remaining portions of the current image.

* * * * *